(12) United States Patent
Wang et al.

(10) Patent No.: US 11,459,553 B2
(45) Date of Patent: Oct. 4, 2022

(54) STRAIN FOR PRODUCING CHITINASE AND APPLICATION THEREOF

(71) Applicant: CHANGSHU INSTITUTE OF TECHNOLOGY, Suzhou (CN)

(72) Inventors: Limei Wang, Suzhou (CN); Tiantian Xu, Suzhou (CN); Bin Qi, Suzhou (CN)

(73) Assignee: CHANGSHU INSTITUTE OF TECHNOLOGY, Suzhou (CN)

( * ) Notice: Subject to any disclaimer, the term of this patent is extended or adjusted under 35 U.S.C. 154(b) by 9 days.

(21) Appl. No.: 16/975,415

(22) PCT Filed: Oct. 31, 2019

(86) PCT No.: PCT/CN2019/114751
§ 371 (c)(1),
(2) Date: Aug. 25, 2020

(87) PCT Pub. No.: WO2020/103668
PCT Pub. Date: May 28, 2020

(65) Prior Publication Data
US 2021/0002684 A1    Jan. 7, 2021

(30) Foreign Application Priority Data
Nov. 19, 2018   (CN) .................. 201811376356.X

(51) Int. Cl.
| | | |
|---|---|---|
| *C12N 9/26* | (2006.01) | |
| *C12P 19/14* | (2006.01) | |
| *C12N 9/42* | (2006.01) | |
| *C12P 19/04* | (2006.01) | |
| *C12N 1/20* | (2006.01) | |
| *C12R 1/465* | (2006.01) | |

(52) U.S. Cl.
CPC ............ *C12N 9/2442* (2013.01); *C12N 1/205* (2021.05); *C12P 19/04* (2013.01); *C12P 19/14* (2013.01); *C12R 2001/465* (2021.05)

(58) Field of Classification Search
CPC ........ C12N 9/2442; C12N 1/205; C12P 19/14
See application file for complete search history.

(56) References Cited

U.S. PATENT DOCUMENTS 4,686,185 A * 8/1987 Wakunaga ............. C12N 1/205
                                                           435/206

FOREIGN PATENT DOCUMENTS

CN          109337843 A    2/2019

* cited by examiner

*Primary Examiner* — Yong D Pak
(74) *Attorney, Agent, or Firm* — PROI Intellectual Property US; Klaus Michael Schmid

(57) ABSTRACT

The present invention relates to a strain for producing chitinase and application thereof. The class of the strain is named *Streptomyces diastaticus* CS1801 and the preservation number thereof is CCTCC NO: M2018263. The *Streptomyces diastaticus* CS1801 of the present invention is derived from naturally fermented prawn paste. By fermentation of prawns, the enzyme activity of the chitosan is as high as 57.3 U/L and the content of chitooligosaccharides is 0.58 mol/L. The present invention provides a new method for producing chitooligosaccharides and has a good application prospect.

12 Claims, 3 Drawing Sheets

Specification includes a Sequence Listing.

SEQUENCE LISTING

```
<160> NUMBER OF SEQ ID NOS: 1

<210> SEQ ID NO 1
<211> LENGTH: 1431
<212> TYPE: DNA
<213> ORGANISM: Streptomyces diastaticusCS1801

<400> SEQUENCE: 1
gggtggcggg gtgctttacc atgcagtcga acgatgaagc ccttcggggt ggattagtgg      60
cgaacgggtg agtaacacgt gggcaatctg ccctgcactc tgggacaagc cctggaaacg     120
gggtctaata ccggatatga ccgtccatcg catggtggat ggtgtaaagc tccggcggtg     180
caggatgagc ccgcggccta tcagctagtt ggtgaggtag tggctcacca aggcgacgac     240
gggtagccgg cctgagaggg cgaccggcca cactgggact gagacacggc ccagactcct     300
acgggaggca gcagtgggga atattgcaca atgggcgaaa gcctgatgca gcgacgccgc     360
gtgagggatg acggccttcg ggttgtaaac ctctttcagc agggaagaag cgaaagtgac     420
ggtacctgca gaagaagcgc cggctaacta cgtgccagca gccgcggtaa tacgtagggc     480
gcaagcgttg tccggaatta ttgggcgtaa agagctcgta ggcggcttgt cacgtcggtt     540
gtgaaagccc ggggcttaac cccgggtctg cagtcgatac gggcaggcta gagttcggta     600
ggggagatcg gaattcctgg tgtagcggtg aaatgcgcag atatcaggag gaacaccggt     660
ggcgaaggcg gatctctggg ccgatactga cgctgaggag cgaaagcgtg gggagcgaac     720
aggattagat accctggtag tccacgccgt aaacggtggg cactaggtgt gggcaacatt     780
ccacgttgtc cgtgccgcag ctaacgcatt aagtgccccg cctggggagt acggccgcaa     840
ggctaaaact caaaggaatt gacggggggcc cgcacaagcg gcggagcatg tggcttaatt     900
cgacgcaacg cgaagaacct taccaaggct tgacatacac cggaaagcat cagagatggt     960
gccccccttg tggtcggtgt acaggtggtg catggctgtc gtcagctcgt gtcgtgagat    1020
gttgggttaa gtcccgcaac gagcgcaacc cttgtcccgt gttgccagca ggcccttgtg    1080
```

-continued

```
gtgctgggga ctcacgggag accgccgggg tcaactcgga ggaaggtggg gacgacgtca    1140
agtcatcatg cccttatgt cttgggctgc acacgtgcta caatggccgg tacaatgagc     1200
tgcgataccg tgaggtggag cgaatctcaa aaagccggtc tcagttcgga ttggggtctg    1260
caactcgacc ccatgaagtc ggagtcgcta gtaatcgcag atcagcattg ctgcggtgaa    1320
tacgttcccg ggccttgtac acaccgcccg tcacgtcacg aaagtcggta acacccggaa    1380
gccggtggcc caaccccctt gtggggaggg agcgtcgaag tgaatcgggt t             1431
```

STRAIN FOR PRODUCING CHITINASE AND APPLICATION THEREOF

TECHNICAL FIELD

The present invention relates to a strain for producing chitinase and application thereof in fermenting prawns to produce chitooligosaccharides, and pertains to a technology in the field of industrial microorganisms.

Background Technologies

Chitosan, also known as chitin, is a polymer of N-acetyl-D-glucosamine linked by β-1,4 glycosidic bonds, and widely exists in the nature, with reserves ranking second only to cellulose. The water insolubility of chitosan greatly limits the scope of application, but it can be decomposed into water-soluble chitooligosaccharides or chitosan oligosaccharides (COS) under the action of chitinase. The decomposition products of chitosan have a variety of effects such as bacteriostasis, oxidation resistance, and promotion of growth and development of animals and plants. A large number of studies have found that chitosan and COS have significant anti-neuroinflammation and antioxidant effects, and may be widely applied in the treatment of Alzheimer's disease in the future. At the same time, COS also has significant anti-tumor activity, and shows broad application prospects in food, agriculture and medicine.

The organisms producing chitinase mainly largely come from microorganisms, which mainly include *Bacillus, Streptomyces, Serratia marcescens* and *Pseudomonas*. By means of random mutagenesis, site-directed mutagenesis, changing the source of screening, etc., researchers have obtained chitinase with a high yield or special properties, such as cold resistant, heat resistant, and acid and alkali resistant chitinase. Prawn paste is mainly made from ocean prawns through addition of salt and about one month of natural fermentation. It is rich in protein and chitosan. It is a commonly used seasoning in China and Southeast Asia. Prawn paste has very complex microbial diversity and composition, and is suitable for being used to screen strains for producing chitinase. At the same time, prawns are rich in chitosan and low in price, suitable as substrates for chitosan decomposition products and have a strong industrial application prospect. At present, there is no report on screening strains for producing chitinase from prawn paste and using prawns to produce chitooligosaccharides.

SUMMARY

The first objective of the present invention is to provide a strain for producing chitinase.

In order to achieve the foregoing technical objective of the present invention, the present invention adopts the following technical solution:

A strain for producing chitinase, with its class named *Streptomyces diastaticus* CS1801, and preserved at China Center for Type Culture Collection (CCTCC), address: Wuhan University, Wuhan, China, preservation number: CCTCC NO: M2018263, and date of preservation: May 10, 2018. The deposit was made and accepted under the Budapest Treaty and applicants aver under 37 CFR § 1.808(a) that the deposit was made under conditions that assure that:

(1) Access to the deposit will be available during pendency of the patent application making reference to the deposit to one determined by the Director to be entitled thereto under § 1.14 and 35 U.S.C. § 122, and (2) Subject to paragraph (b) of this section, all restrictions imposed by the depositor on the availability to the public of the deposited material will be irrevocably removed upon the granting of the patent.

The strain was isolated from naturally fermented prawn paste.

The physical and chemical properties of *Streptomyces* CS1801 of the present invention are as follows:

Morphology: After growth on a screening medium for 5 to 7 days, obvious colonies can be formed, which are round, dry, coarse, convex and powdery, can be picked easily and have no pigment and a light soil mildew smell. Obvious colonies can be formed on the PDA, too. The colonies are round, dry, coarse, convex and powdery, can hardly be picked, and have dark green pigment and a strong soil mildew smell. Gram-positive bacteria are observed under an electron microscope, the spore chain runs straight or flexible and has branches, and the spores are oval, with a smooth surface.

Cultural characteristics: The optimal temperature for growth is about 30° C., aerobic; and the optimal pH value for growth is 6.5-7.

The second objective of the present invention is to provide an application of the foregoing strain in fermenting prawns to produce chitooligosaccharides.

Further, the present invention provides a few fermentation media that can be used to produce chitooligosaccharides, including:

With colloidal chitosan as a fermentation substrate, the composition of the fermentation medium is as follows:

Liquid A: $K_2HPO_4$ 1.4 g/L, $KH_2PO_4$ 0.6 g/L, $MgSO_4 \cdot 7H_2O$ 1 g/L, NaCl 10 g/L, $(NH_4)_2SO_4$ 20 g/L, deionized water 1000 mL, pH 6.5;

Liquid B: 10 g/L colloidal chitosan, pH 6.5;

Before use, liquid A and liquid B are mixed in an equal volume.

Here, the method for preparing colloidal chitosan is as follows: Weigh 10 g of powdery chitosan, slowly add 200 mL of concentrated hydrochloric acid, stir rapidly, filter the solution with glass wool after thorough dissolution to remove impurities, and add 1,000 mL of distilled water into the solution. Centrifuge to obtain precipitate and wash the precipitate with distilled water till neutral.

Alternatively, with prawn powder as a fermentation substrate, the composition of the fermentation medium is as follows:

Liquid A: $K_2HPO_4$ 1.4 g/L, $KH_2PO_4$ 0.6 g/L, $MgSO_4 \cdot 7H_2O$ 1 g/L, NaCl 10 g/L, $(NH_4)_2SO_4$ 20 g/L, deionized water 1000 mL, pH 6.5;

Liquid B: 100 g/L prawn powder, pH 6.5;

Liquid A and liquid B are mixed in an equal volume.

Here, the method for preparing prawn powder is as follows: defreeze frozen prawns in running water, and bake and pulverize the prawns, and screen the powder through a 100 mesh sieve.

Alternatively, with wet prawns as a fermentation substrate, the composition of the fermentation medium is as follows:

300 g/L wet prawns, pH 6.5.

Here, the wet prawns are obtained by defreezing frozen prawns in running water.

The steps of fermenting a strain to produce chitooligosaccharides are as follows:

(1) Inoculate a strain CS1801 to a PDA liquid medium, and culture it under shaking at 30° C. for 2 to 3 d;

(2) Lead the strain cultured at step (1) to a fermentation medium, and ferment it under shaking at 30 to 37° C. for 5 to 7 d; centrifuge the fermentation liquor, discard the precipitate and take the supernate.

Further, the fermentation culturing at step (2) is performed at 30° C.

The strain of the present invention as a starting strain can biologically catalyze prawns to produce chitooligosaccharides; this strain is derived from traditional naturally fermented food and has a broad application prospect in the food industry; the strain grows well on a PDA solid medium and can be easily cultured and preserved. The enzyme activity of chitinase obtained by fermenting prawns can reach 57.3 U/L and the content of chitooligosaccharides is 0.58 mol/L.

The biological material that the present invention relates to, with its class named *Streptomyces diastaticus* CS1801, preserved at China Center for Type Culture Collection (CCTCC), address: Wuhan University, Wuhan, China, preservation number: CCTCC NO: M2018263, and date of preservation: May 10, 2018.

DETAILED DESCRIPTION

Embodiment 1

This embodiment describes methods for screening, purifying and identifying *Streptomyces diastaticus* CS1801.

The screening sample is prawn paste of Lianyungang Haiwa Food Co., Ltd. 25 g of the prawn paste and 225 mL of normal saline are taken to prepare a bacterial suspension, and the suspension is diluted by $10^{-1}$, $10^{-2}$, $10^{-3}$ and $10^{-4}$ times respectively. The original bacterial suspension, $10^{-1}$ diluted bacterial suspension, $10^{-2}$ diluted bacterial suspension, $10^{-3}$ diluted bacterial suspension and $10^{-4}$ diluted bacterial suspension are spread on the primary screening medium respectively. After growth at 37° C. for 1 to 7 d, single colony, which grows well, is picked, and lines are drawn on the primary screening medium for isolation. A single colony produced on the primary screening medium and having an obvious transparent circle around it is picked, inoculated to a liquid medium and cultured in a 37° C., 200 r/min shaker for 1 to 7 d. Primary screening medium: Liquid A: $K_2HPO_4$ 1.4 g/L, $KH_2PO_4$ 0.6 g/L, $MgSO_4 \cdot 7H_2O$ 1 g/L, NaCl 10 g/L, $(NH_4)_2SO_4$ 20 g/L, agar 40 g/L, deionized water 1000 mL, pH 6.5. Liquid B: 10 g/L colloidal chitosan, pH 6.5. Before use, liquid A and liquid B are mixed in an equal volume.

Secondary screening medium: Liquid A: $K_2HPO_4$ 1.4 g/L, $KH_2PO_4$ 0.6 g/L, $MgSO_4 \cdot 7H_2O$ 1 g/L, NaCl 10 g/L, $(NH_4)_2SO_4$ 20 g/L, deionized water 1000 mL, pH 6.5. Liquid B: 10 g/L colloidal chitosan, pH 6.5. Before use, liquid A and liquid B are mixed in an equal volume.

Figure 1:
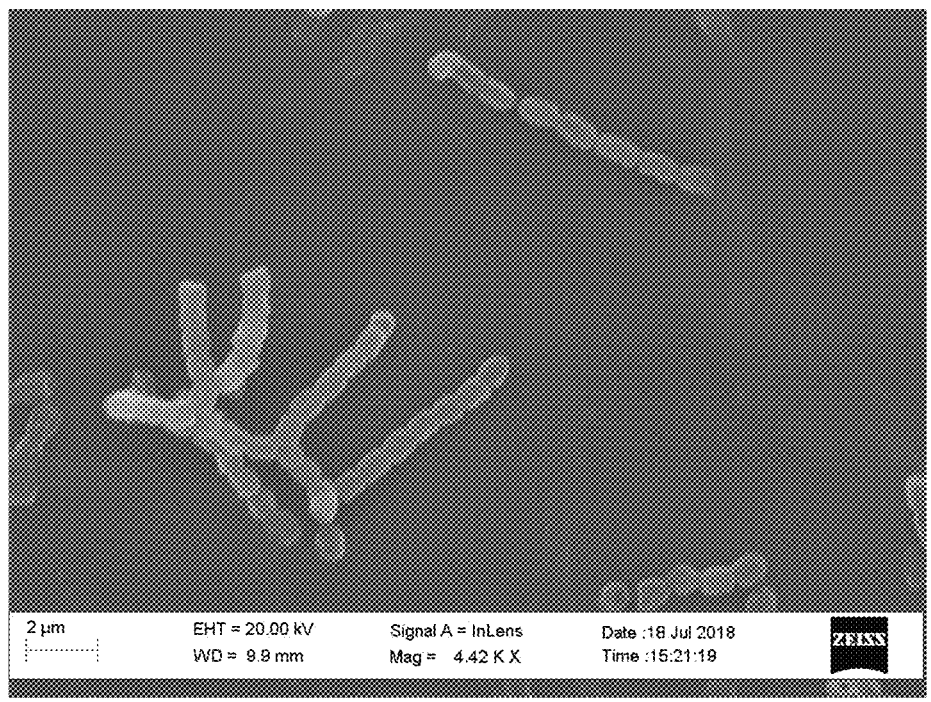
FIG. 1 is an image of *Streptomyces diastaticus* CS1801 observed under an electron microscope.

A slide is inserted on the PDA solid medium and cultured for 7 days. Then the slide is cut to a suitable size, directly sprayed with gold and scanned, and observed under an electron microscope. The spore chain runs straight or flexible and has branches, and the spores are oval, with a smooth surface (FIG. 1).

Figure 2:
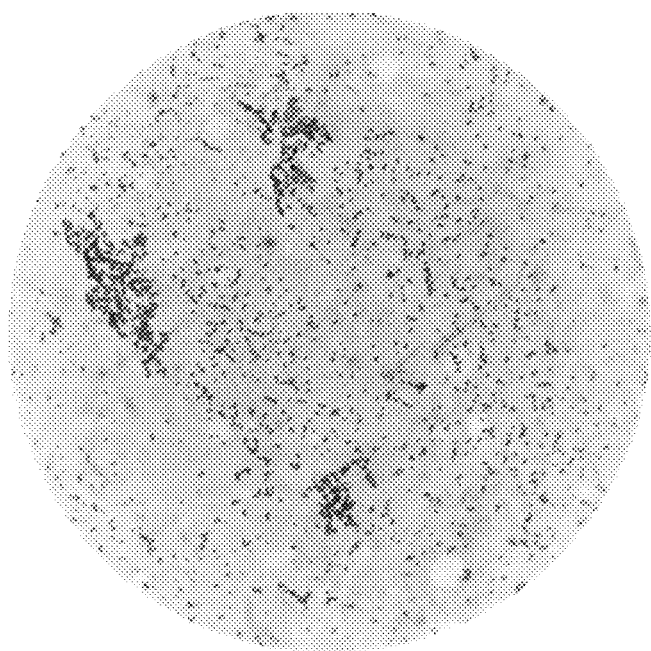
FIG. 2 is microscopic morphology of *Streptomyces diastaticus* CS1801 after Gram staining.

A ring of bacteria are picked from the primary screening medium plate, mixed with the water beads on the slide and quenched. After primary staining by crystal violet, enzyme staining by an iodine solution, decoloring by ethanol and counterstaining by safflower, the bacteria are observed under a microscope. The bacteria are Gram negative bacteria (FIG. 2).

Figure 3:
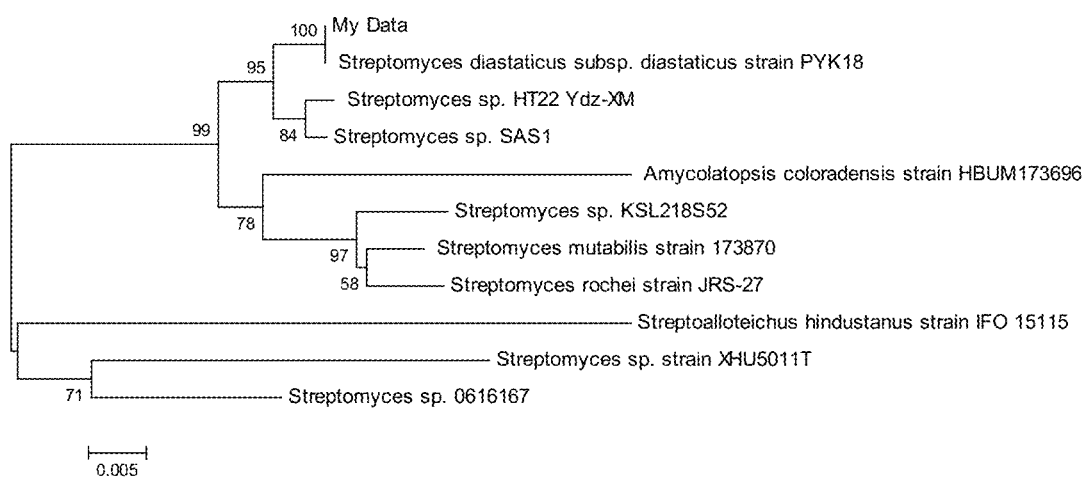
FIG. 3 is a phylogenetic tree of *Streptomyces diastaticus* CS1801.

After determination of the sequence of 16SrDNA part of the foregoing strain and BLAST comparison, MEGA 5.1 is used to construct N-J phylogenetic tree for analysis, its 16SrDNA sequence is as shown in SEQ ID NO.1, and the phylogenetic tree is as shown in FIG. 3. Thus it is identified as *Streptomyces*, and after the identification and preservation of the microorganism preservation program, its class is named *Streptomyces diastaticus* CS1801, and its preservation number is CCTCC M2018263.

Embodiment 2

This embodiment specifically describes the application of strain CS1801 for producing chitooligosaccharides through fermentation by colloidal chitosan.

(1) Inoculate a strain CS1801 to a PDA liquid medium, and culture it under shaking at 30° C. for 2 to 3 d; and (2) Lead the strain cultured at step (1) to a fermentation medium, and culture it under shaking at 30° C. for 7 d; centrifuge the fermentation liquor to discard the precipitate and take the supernate, and determine the enzyme activity of chitinase is 117.4 U/L, and the content of chitooligosaccharides is 1.18 mol/L.

The composition of the fermentation medium is the same as that of the foregoing secondary screening medium.

The method for determining enzyme activity of chitinase is as follows: The fermentation liquor is centrifuged at 3000 r for 10 min, and the supernate is taken as a test sample. The test sample, horse radish peroxidase (HRP)-labeled detection antibody are added in turn into the micropores that are coated with chitinase antibody in advance, cultured at 37° C. for 1 h and then thoroughly washed. Color development is performed using substrate 3,3',5,5'-tetramethyl benzidine (TMB) and the color turns blue under the catalysis of HRP and turns yellow in the end under the action of acid. The OD value at 450 nm is measured with a microplate reader, and the sample activity is calculated through a standard curve. The standard substances are 0, 1.5, 3, 6, 12, 24 U/L enzyme solutions prepared from pure chitinase. The enzyme activity is defined as: at 37° C., the amount of enzyme that decomposes chitosan per mg of protein per hour to produce 1 mg of N-acetylglucosamine is an enzyme activity unit U. The chitinase ELISA detection kit was purchased from Wuhan Chundu Biotechnology Co., Ltd.

Embodiment 3

This embodiment specifically describes the types of products of chitooligosaccharides produced from strain CS1801 through fermentation by colloidal chitosan.

(1) Inoculate a strain CS1801 to a PDA liquid medium, and culture it under shaking at 30° C. for 2 to 3 d; and (2) Lead the strain cultured at step (1) to a fermentation medium, and culture it under shaking at 30° C. for 7 d; centrifuge the fermentation liquor to discard the precipitate and take the supernate.

The composition of the fermentation medium is the same as that of the foregoing secondary screening medium.

Figure 4:
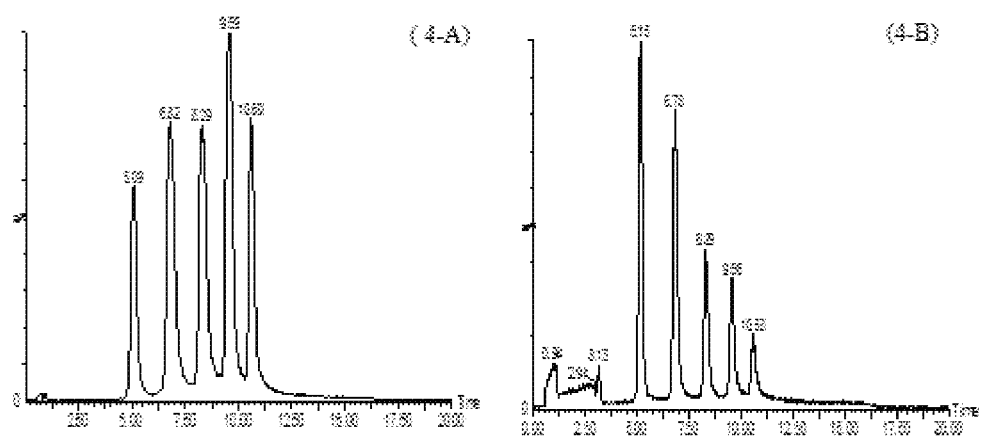
FIG. 4 is an ultra high performance liquid chromatogram of a fermentation liquor of *Streptomyces diastaticus* CS1801, where 4-A is a liquid chromatogram of a standard substance, and 4-B is a liquid chromatogram of the fermentation liquor.
Figure 5:
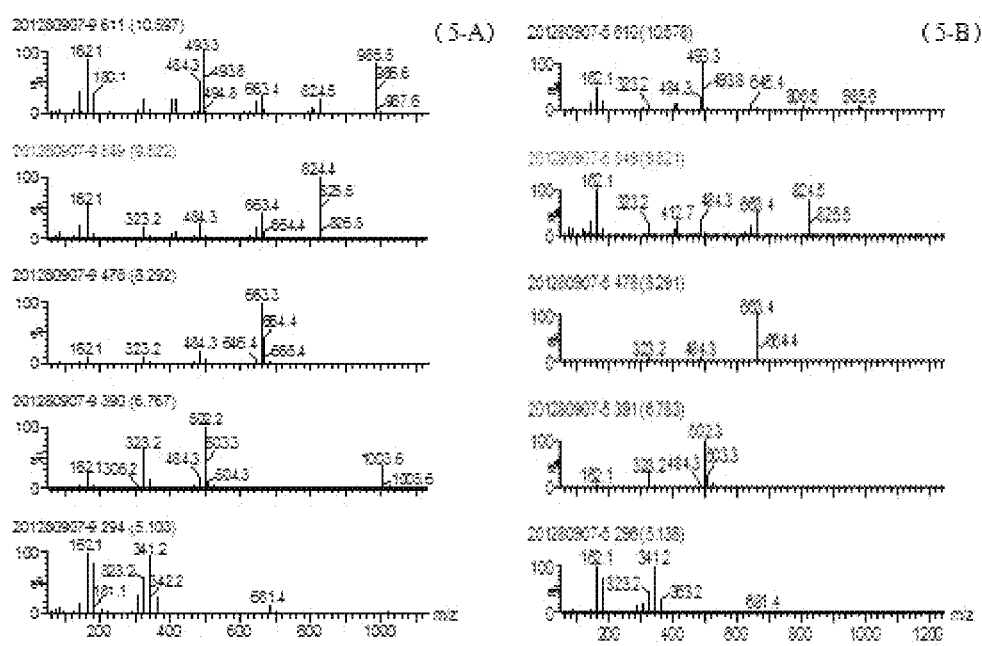
FIG. 5 is a mass spectrum of a fermentation liquor of *Streptomyces diastaticus* CS1801, where 5-A is a mass spectrum of a standard substance, and 5-B is a mass spectrum of the fermentation liquor.

The composition of the fermentation liquor is analyzed by ultra-high performance liquid chromatography-mass spectrum (UPLC-Q-TOF-MS) technology to determine that chitosan is decomposed into chitobiose, chitotriose, chitotetraose, chitopentaose and chitohexaose under the action of *Streptomyces* CS1801. The ultra-high performance liquid chromatogram is shown in FIG. 4, and the mass spectrum is shown in FIG. 5.

Embodiment 4

This embodiment specifically describes the application of strain CS1801 for producing chitooligosaccharides through fermentation by prawn powder.

(1) Inoculate a strain CS1801 to a PDA liquid medium, and culture it under shaking at 30° C. for 2 to 3 d; and (2) Lead the strain cultured at step (1) to a fermentation medium, and ferment it under shaking at 35° C. for 5 d; centrifuge the fermentation liquor to discard the precipitate and take the supernate, and determine the enzyme activity of chitinase is 57.3 U/L, and the content of chitooligosaccharides is 0.58 mol/L. The enzyme activity of chitinase is determined as described in Embodiment 2.

The fermentation medium is as follows:

Liquid A: $K_2HPO_4$ 1.4 g/L, $KH_2PO_4$ 0.6 g/L, $MgSO_4 \cdot 7H_2O$ 1 g/L, NaCl 10 g/L, $(NH_4)_2SO_4$ 20 g/L, deionized water 1000 mL, pH 6.5. Liquid B: 100 g/L prawn powder, pH 6.5. Liquid A and liquid B are mixed in an equal volume.

Embodiment 5

This embodiment specifically describes the application of strain CS1801 for producing chitooligosaccharides through fermentation by wet prawns.

(1) Inoculate a strain CS1801 to a PDA liquid medium, and culture it under shaking at 30° C. for 2 to 3 d;

(2) Lead the strain cultured at step (1) to a fermentation medium, and ferment it under shaking at 37° C. for 7 d; centrifuge the fermentation liquor to discard the precipitate and take the supernate, and determine the enzyme activity of chitinase is 50.3 U/L, and the content of chitooligosaccharides is 0.43 mol/L. The enzyme activity of chitinase is determined as described in Embodiment 2.

The fermentation medium is as follows: 300 g/L wet prawns, pH 6.5.

What is claimed is:

1. A strain for producing chitinase, where the strain is *Streptomyces diastaticus* CS1801 and the preservation number thereof is CCTCC NO: M2018263.

2. A method for production of chitooligosaccharides, comprising: admixing *Streptomyces diastaticus* CS1801 with the preservation number CCTCC NO: M2018263 with a chitosan-containing substrate in a fermentation medium to produce a mixture; and
fermenting the mixture for a time sufficient to produce chitooligosaccharides.

3. The method for production of chitooligosaccharides according to claim 2, wherein the fermenting the mixture is at a temperature of 30° C., and pH 6.5-7.

4. The method for production of chitooligosaccharides according to claim 2, wherein the fermentation medium is:
liquid A: $K_2HPO_4$ 1.4 g/L, $KH_2PO_4$ 0.6 g/L, $MgSO_4.7H_2O$ 1 g/L, NaCl 10 g/L, $(NH_4)_2SO_4$ 20 g/L, deionized water 1000 mL, pH 6.5;
and the chitosan-containing substrate is: liquid B: 10 g/L colloidal chitosan, pH 6.5;
wherein, liquid A and liquid B are mixed in an equal volume.

5. The method for production of chitooligosaccharides according to claim 4, wherein the colloidal chitosan is prepared as follows: weigh 10 g of powdery chitosan, add 200 mL of concentrated hydrochloric acid, stir, filter the solution with glass wool after thorough dissolution to remove impurities, and add 1,000 mL of distilled water into the solution, centrifuge to obtain a precipitate and wash the precipitate with distilled water till neutral.

6. The method according to claim 2, wherein the fermentation medium is:
liquid A: $K_2HPO_4$ 1.4 g/L, $KH_2PO_4$ 0.6 g/L, $MgSO_4.7H_2O$ 1 g/L, NaCl 10 g/L, $(NH_4)_2SO_4$ 20 g/L, deionized water 1000 mL, pH 6.5;
and the chitosan-containing substrate is: liquid B: 100 g/L prawn powder, pH 6.5;
wherein liquid A and liquid B are mixed in an equal volume.

7. The method according to claim 6, wherein the prawn powder is prepared as follows: defrost frozen prawns bake; pulverize the prawns to produce a powder, and sieve the powder through a 100 mesh sieve.

8. The method according to claim 2, wherein the chitosan-containing substrate is: 300 g/L wet prawns, pH 6.5.

9. The method according to claim 2, further comprising:
(1) inoculating strain CS1801 into a PDA liquid medium, and culturing it under shaking at 30° C. for 2 to 3 d;
(2) mixing the strain cultured at step (1) and the fermentation medium, and fermenting under shaking at 30 to 37° C. for 5 to 7 d to create a fermentation liquor; centrifuging the fermentation liquor, discarding the precipitate and collecting the supernate containing chitooligosaccharides.

10. The method according to claim 9, wherein the temperature of fermenting and culturing is 30° C.

11. The method according to claim 2, wherein the fermenting the mixture is at a temperature of 30° C., and pH 6.5-7.

12. The method of claim 8 wherein the wet prawns are prepared by defrosting frozen prawns.

* * * * *